United States Patent [19]
Vaillancourt et al.

[11] Patent Number: 4,682,607
[45] Date of Patent: Jul. 28, 1987

[54] WIRE GUIDE

[75] Inventors: Vincent L. Vaillancourt, Livingston; Stephen Kocanowski, Middlesex, both of N.J.

[73] Assignee: VLV Associates, East Hanover, N.J.

[21] Appl. No.: 803,719

[22] Filed: Dec. 2, 1985

[51] Int. Cl.4 .............................................. A61M 25/00
[52] U.S. Cl. ..................... 128/772; 128/657; 604/95
[58] Field of Search .............................. 128/656–658, 128/772, 341; 604/95, 170, 280

[56] References Cited

U.S. PATENT DOCUMENTS

| | | | |
|---|---|---|---|
| 2,221,138 | 11/1940 | Hendrickson | 128/341 |
| 3,612,058 | 10/1971 | Ackerman | 128/772 |
| 4,504,268 | 3/1985 | Herlitze | 604/170 |
| 4,538,622 | 9/1985 | Samson et al. | 128/772 |
| 4,579,127 | 4/1986 | Haake | 128/772 |

*Primary Examiner*—Dalton L. Truluck
*Attorney, Agent, or Firm*—Kenyon & Kenyon

[57] ABSTRACT

The wire guide is formed of a flexible stranded wire having a coating extending from the proximal end to rigidify the wire from the proximal end to an intermediate point. The wire remains flexible from the intermediate point to the distal end and a nose is fused to the distal end to prevent fraying of the filaments of the wire.

12 Claims, 4 Drawing Figures

U.S. Patent   Jul. 28, 1987   4,682,607
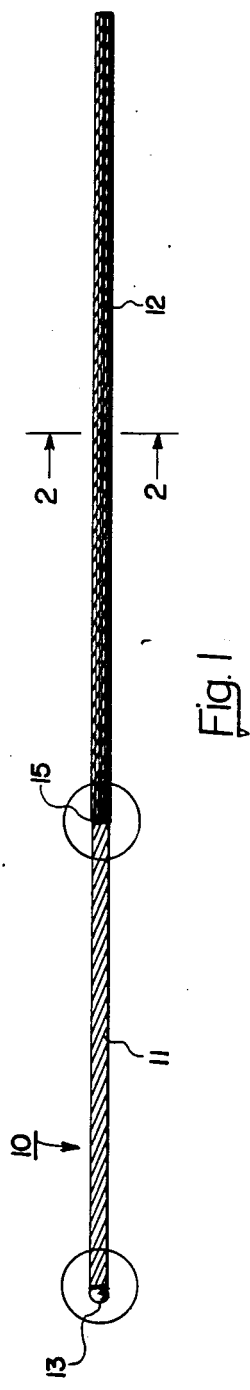
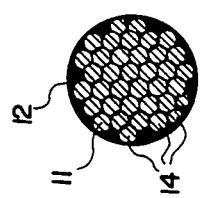
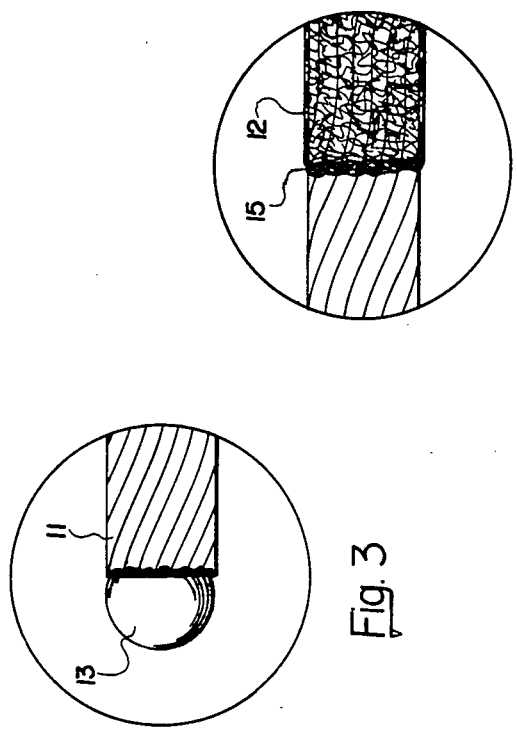
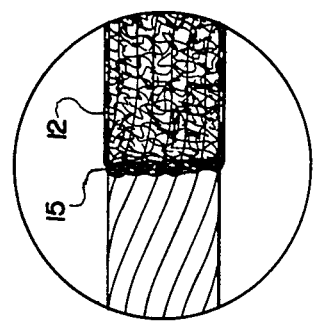

WIRE GUIDE

This invention relates to a wire guide. More particularly, this invention relates to a wire guide for a catheter.

Heretofore, various types of wire guides have been used for implantation in the vascular system of the human body. Generally, these wire guides require a flexible distal section to avoid damage to the vascular tissue as well as a rigid section to enable the wire guide to be directed to a desired location within the vascular system. For example, U.S. Pat. No. 3,612,058 describes a wire guide which includes an outer casing formed of a continuous helical coil of hardened stainless steel strength wire which is reinforced internally by a stainless steel tubing which extends within a rigid section. In addition, a strand of stainless steel wire or cable is provided to act as a reinforcing means between a plastic tip and the tubing in order to pull the tip from a vessel should the wire guide break therein. However, such a wire guide is relatively cumbersome and expensive to manufacture.

It has also been known from U.S. Pat. No. 3,789,841 to construct a wire guide with a coil spring which extends only over a flexible section without extending over a rigid section. In this case, the rigid section is formed by a core wire of uniform thickness which is coated with a plastic jacket while the flexible section is formed by a tapered portion of the core wire and a surrounding a coil spring. The use of the plastic jacket is said to eliminate the need for the coil spring to extend over the entire length of guide wire and thus reduces the amount of the spring material required. While the cost of the guide wire may be reduced, the overall costs and manufacturing techniques to produce this wire guide remains relatively expensive.

Accordingly, it is an object of the invention to provide a wire guide which can be easily manufactured at a minimal cost.

It is an another object of the invention to provide a wire guide which can be manufactured with relatively simple techniques.

Briefly, the invention provides a wire guide which is comprised of a length of stranded wire having a flexible section extending to a distal end and a rigid section extending from the flexible section to a proximal end and a nose at the distal end of the wire.

The wire guide is constructed so that the stranded wire, for example being made of individual stainless steel filaments which are twisted together, has a flexible section at the distal end so as to be able to negotiate twists and turns, for example when implanted in a vessel. To this end, the flexible section has a diameter of about 0.008 inches to 0.062 inches.

The nose which is provided at the distal end of the wire is of any suitable shape such as a spherical shape and is disposed over at distal end of the wire in order to preclude the wire from fraying.

The rigid section of the stranded wire may be formed by having a coating thereon which extends from the flexible section to the proximal end of the wire. For example, the coating may be made of an epoxy or any other suitable material which is able to rigidify the wire to a sufficient extent to permit manipulation into a vessel.

These and other objects and advantages of the invention will become more apparent from the following detailed description taken in conjunction with the accompanying drawings wherein:

FIG. 1 illustrates a side view of a wire guide constructed in accordance with the invention;

FIG. 2 illustrates a cross sectional view taken on line II—II of FIG. 1;

FIG. 3 illustrates an enlarged view of the nose of the wire guide; and

FIG. 4 illustrates an enlarged view of the junction between the flexible section and rigid section of the wire guide.

Referring to FIG. 1, the wire guide 10 is formed of a length of stranded wire 11, a coating 12 and a nose 13 at the distal end of the wire 10.

As indicated in FIGS. 1 and 2, the stranded wire 11 is composed of a plurality of individual filaments 14, for example of stainless steel or any other suitable biocompatible material. These filaments 14 are twisted in conventional fashion to form a unitary strand. For example, the wire 11 may have a diameter of from about 0.008 inches to 0.062 inches.

The coating 12 is made of an epoxy or any other suitable material and extends from an intermediate point 15 to the proximal end of the wire guide 10. As indicated in FIG. 4, the coating 12 defines a slightly tapered end at the intermediate point 15. For example, the epoxy may be a low temperature curing epoxy adhesive sold by Amicon, a division of W. R. Grace and Company under the mark UNISET® 910-22. This epoxy may be applied by dipping of the stranded wire 11 in the epoxy to the desired thickness, followed by squeezing off the excess and then curing the wire in an oven for ten minutes at 100° C.

The nose 13 is made of an element separate from the stranded wire 11 and may be of any suitable material, such as a tin-silver metal, tin-gold metal or the like and is of any suitable shape such as a spherical shape. As indicated in FIG. 3, the nose 13 is made from a spherical metal ball of solid construction which has been fused to the end of the wire 11 in any suitable fashion. For example, an acid flux may be applied to the distal end of the wire 11 while the spherical metal ball is heated and applied against the distal end of the wire 11. Upon cooling, the ball becomes fused to the wire 11 so as to form the nose 13 in the shape indicated in FIG. 3 and, as such, protects the wire 11 from fraying at the distal end.

Alternatively, the nose 13 may be formed from the stranded wire 11 using a suitable welding process, such as a heli-arc or plasma process. In this case, a spherical shape is also formed on the end of the stranded wire 11.

Referring to FIG. 1, the wire guide thus has a flexible section which extends from the distal end to the intermediate point 15 as well as a rigid section which extends from the intermediate point 15 to the proximal end. As such, the wire guide 10 can be used in any suitable manner, for implantation within a vessel of a human body. For example, the wire guide can be used for the introduction of a catheter using the well known Seldinger technique, for example as described in U.S. Pat. No. 3,789,841. To this end, the wire strand 11 may have a diameter of 0.018 inches so as to be used, for example to guide a catheter having an inside diameter of 0.23 inches.

For manipulation purposes, for example, for use as an angiographic wire guide, the end of the flexible section may be pre-bent in a "J" shape. This allows for wire guide steering during placement. Further, due to the stranded construction of the wire guide, as opposed to a spring wire, a better (more) torque control can be exerted during manipulation.

The wire guide 10 may also be provided with a polymer coating, such as Teflon, silicon or hydrophillic material such as polyvinylpyrrilodone, polyurethane or hydroxyethyl methacrylate at a distal end or over the entire length to provide a smooth biocompatible surface for insertion into a vessel while providing a totally encapsulated flexible section which minimizes the tendency for blood clots, and the like, to form. That is, a continuous surface is provided without openings into which matter, such as blood, may collect.

The invention thus provides a wire guide which has a flexible section which permits introduction into the vascular system of a human body, for example, for percutaneous vascular catheterization. Further, the wire guide has a rigid section which permits easy manipulation of the wire guide.

Since the wire guide is made of a minimum of parts, the risk of any one part breaking off within the vascular system is reduced. Further, the manufacturing techniques required to make wire guides are greatly simplified.

What is claimed is:

1. A wire guide for a catheter comprising a length of stranded wire having a flexible section of a diameter of from about 0.008 inches to 0.062 inches extending to a distal end and a rigid section extending from said flexible section to a proximal end and a nose at said distal end of said wire.

2. A wire guide as set forth in claim 1 wherein said nose has a spherical shape.

3. A wire guide as set forth in claim 1 having a polymer coating over at least said flexible section to form a smooth biocompatible surface.

4. A wire guide for a catheter comprising
   a length of stranded wire having a flexible section extending to a distal end and a rigid section extending from said flexible section to a proximal end; and
   a metal nose of spherical shape fused to said distal end of said flexible section of said wire.

5. A wire guide as set forth in claim 4 wherein said flexible section has a diameter of from about 0.008 inches to 0.062 inches.

6. A wire guide for a catheter comprising
   a flexible length of stranded wire;
   a coating on a section of said wire extending from a proximal end to an intermediate point to rigidify said section; and
   a nose on a distal end of said wire to protect said wire from fraying at said distal end.

7. A wire guide as set forth in claim 6 wherein said wire is made of stainless steel.

8. A wire guide as set forth in claim 6 wherein said coating is an epoxy.

9. A wire guide as set forth in claim 6 wherein said nose has a spherical shape and is made of metal.

10. A wire guide as set forth in claim 6 wherein said wire has a diameter of about 0.008 inches to 0.062 inches.

11. A wire guide as set forth in claim 6 having a polymer coating at least over a distal end thereof to form a smooth biocompatible surface.

12. A wire guide comprising
    a length of stainless steel stranded wire of a diameter of from about 0.008 inches to 0.062 inches;
    an epoxy coating on a section of said wire extending from a proximal end to an intermediate point to rigidify said section; and
    a spherical metal nose integral with said wire at a distal end thereof to retain said wire from fraying thereat.

* * * * *

UNITED STATES PATENT AND TRADEMARK OFFICE
CERTIFICATE OF CORRECTION

PATENT NO. : 4,682,607

DATED : July 28, 1987

INVENTOR(S) : Vincent L. Vaillancourt, et al

It is certified that error appears in the above-identified patent and that said Letters Patent is hereby corrected as shown below:

Column 1, line 31 "surrounding a coil" should be -surrounding coil-
Column 1, line 41 "is an another" should be -is another
    or:
    a further
Column 1, line 58 "at" should be -the- Signed and Sealed this Second Day of February, 1988

Attest:

DONALD J. QUIGG

Attesting Officer      Commissioner of Patents and Trademarks